United States Patent
Beliaev et al.

(10) Patent No.: US 8,710,239 B2
(45) Date of Patent: Apr. 29, 2014

(54) PROCESS FOR PREPARING SYNTHETIC INTERMEDIATES OF PERIPHERALLY-SELECTIVE INHIBITORS OF DOPAMINE-β-HYDROXYLASE INVOLVING CATALYTIC ASYMMETRIC HYDROGENATION

(75) Inventors: Alexander Beliaev, Mindelo (PT); David Alexander Learmonth, Alfena (PT)

(73) Assignee: Bial—Portela & C.A., S.A., S. Mamede do Coronado (PT)

( * ) Notice: Subject to any disclaimer, the term of this patent is extended or adjusted under 35 U.S.C. 154(b) by 493 days.

(21) Appl. No.: 12/990,918

(22) PCT Filed: May 6, 2009

(86) PCT No.: PCT/PT2009/000025
§ 371 (c)(1),
(2), (4) Date: Jun. 1, 2011

(87) PCT Pub. No.: WO2009/136803
PCT Pub. Date: Nov. 12, 2009

(65) Prior Publication Data
US 2011/0237803 A1    Sep. 29, 2011

Related U.S. Application Data

(60) Provisional application No. 61/050,754, filed on May 6, 2008.

(51) Int. Cl.
C07D 405/04    (2006.01)
C07D 233/84    (2006.01)
C07D 487/04    (2006.01)

(52) U.S. Cl.
CPC ............ C07D 405/04 (2013.01); C07D 233/84 (2013.01); C07D 487/04 (2013.01)
USPC ................... 548/303.1; 548/311.4; 548/325.1

(58) Field of Classification Search
None
See application file for complete search history.

(56) References Cited

FOREIGN PATENT DOCUMENTS

| WO | 2004033447 | A1 | 4/2004 |
|---|---|---|---|
| WO | 2008071951 | A2 | 6/2008 |
| WO | 2008071951 | A3 | 6/2008 |
| WO | 2009136803 | A2 | 11/2009 |
| WO | 2009136803 | A3 | 11/2009 |

OTHER PUBLICATIONS

Dupau, Philippe, et al., "Direct preparation of N-(alk-1-en-1-yl) carbamates from cyclic ketones and unsubstituted carbamates," Collection of Czechoslovak Chemical Communications, 2002, vol. 67, pp. 235-244.
Dupau, Philippe, et al., "New route to optically active amine derivatives: ruthenium-catalyzed enantioselective hydrogenation of ene carbamates," Tetrahedron: Asymmetry, 1999, vol. 10, pp. 3467-3471, Elsevier Science Ltd., XP-002476034.
Dupau, Philippe, et al., "Synthesis of optically active 2-aminotetraline derivatives via enantioselective ruthenium-catalyzed hydrogenation of ene carbamates," Tetrahedron: Asymmetry, 2001, vol. 12, pp. 863-867, Elsevier Science Ltd., XP002528840.
Greene, Theodora W., et al., Protective Groups in Organic Synthesis, Oct. 1991, 2nd edition, pp. 315-348, John Wiley & Sons, Inc.
Foreign communication from the priority application—International Search Report and Written Opinion, PCT/PT2009/000025, May 20, 2010, 16 pages.
Foreign communication from the priority application—International Preliminary Report on Patentability, PCT/PT2009/000025, Nov. 9, 2010, 7 pages.

*Primary Examiner* — Michael Barker
(74) *Attorney, Agent, or Firm* — Conley Rose, P.C.; Rodney B. Carroll

(57) ABSTRACT

A process for preparing the S or R enantiomer of a compound of formula A,

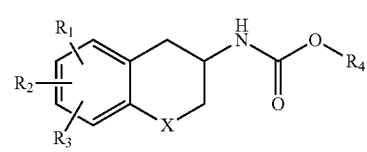

the process comprising subjecting a compound of formula B to asymmetric hydrogenation in the presence of a chiral catalyst and a source of hydrogen,

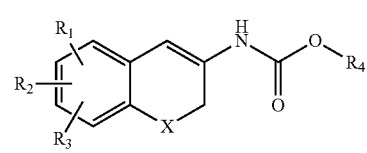

wherein X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine.

21 Claims, No Drawings

PROCESS FOR PREPARING SYNTHETIC INTERMEDIATES OF PERIPHERALLY-SELECTIVE INHIBITORS OF DOPAMINE-β-HYDROXYLASE INVOLVING CATALYTIC ASYMMETRIC HYDROGENATION

CROSS-REFERENCE TO RELATED APPLICATIONS

This application is a filing under 35 U.S.C. 371 of International Application No. PCT/PT2009/000025 filed May 6, 2009, entitled "Process," which is a non-provisional of and claims priority to U.S. Provisional Patent Application No. 61/050,754 filed on May 6, 2008, which applications are incorporated by reference herein in their entirety.

BACKGROUND OF THE INVENTION

The present invention relates to an improved catalytic process for asymmetric hydrogenation. In particular, the present invention relates to a process for preparing intermediates useful in the synthesis of peripherally-selective inhibitors of dopamine-β-hydroxylase (DβH), the process involving catalytic asymmetric hydrogenation.

(R)-5-(2-Aminoethyl)-1-(6,8-difluorochroman-3-yl)-1,3-dihydroimidazole-2-thione hydrochloride (the compound of formula P, below) is a potent, non-toxic and peripherally selective inhibitor of DβH, which can be used for treatment of certain cardiovascular disorders. Compound P is disclosed in WO 2004/033447, along with processes for its preparation.

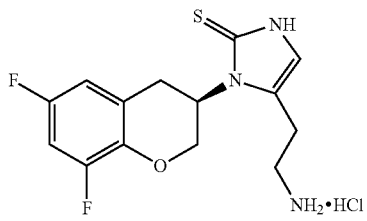

P

The process disclosed in WO 2004/033447 involves the reaction of (R)-6,8-difluorochroman-3-ylamine hydrochloride (the structure of (R)-6,8-difluorochroman-3-ylamine is shown below as compound Q), [4-(tert-butyldimethylsilanyloxy)-3-oxobutyl]carbamic acid tert-butyl ester and potassium thiocyanate.

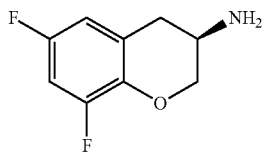

Q (R)-6,8-difluorochroman-3-ylamine (compound Q) is a key intermediate in the synthesis of compound P. The stereochemistry at the carbon atom to which the amine is attached gives rise to the stereochemistry of compound P, so it is advantageous that compound Q is present in as pure a form as possible. In other words, the R enantiomer of compound Q should be in predominance, with little or no S enantiomer present. Thus, the process for preparing compound Q will advantageously produce compound Q with as high an enantiomeric excess (ee) as possible.

An advantageous process for preparing a precursor of, for example, the compound of formula Q has now been found. The process involves catalytic asymmetric hydrogenation of a corresponding novel ene-carbamate. The process may also be employed in the preparation of similar precursors useful in the production of other peripherally-selective inhibitors of dopamine-β-hydroxylase.

The hydrogenation of ene-carbamates using Ru-BINAP and Ru-DuPhos catalysts is described in Dupau, P.; Bruneau, C.; Dixneuf, P. H. *Tet. Asymm.* 1999, 10, 3467-3471; and in Dupau, P.; Hay, A.-E.; Bruneau, C.; Dixneuf, P. H. *Tet. Asymm.* 2001, 12, 863. The maximum ee's obtained with either system are up to 76 (92 for one particular substrate), using a substrate/catalyst ratio of 100/1 and a hydrogen pressure of 100 bar.

BRIEF SUMMARY OF THE INVENTION

According to a first aspect of the present invention, there is provided a process for preparing the S or R enantiomer of a compound of formula A,

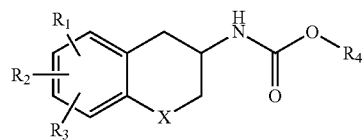

A the process comprising subjecting a compound of formula B to asymmetric hydrogenation in the presence of a chiral catalyst and a source of hydrogen,

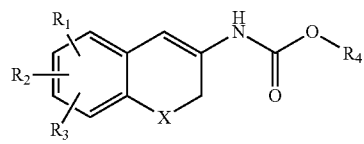

B wherein X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine. Compound B may be referred to as an ene-carbamate. Preferably, the chiral catalyst comprises a ligand which is the S or R enantiomer of TolBINAP and the reaction is carried out at a temperature from above 70° C. to 100° C. and in the presence of an acid at a concentration of 0.05 to 0.2%.

DETAILED DESCRIPTION OF THE INVENTION

Throughout the specification, unless stated otherwise, the terms 'alkoxy' and 'alkyloxy' are equivalent.

In an embodiment, X is O. In another embodiment, at least one of $R_1$, $R_2$ and $R_3$ is fluorine. Suitably, compound A has the following formula:

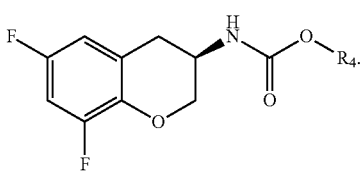

In an embodiment, $R_4$ is $C_1$ to $C_4$ alkyl. Optionally, $R_4$ is methyl (i.e., the methyl-substituted ene-carbamate), ethyl (i.e., the ethyl-substituted ene-carbamate) or tBu (i.e., the tBu-substituted ene-carbamate). Preferably, $R_4$ is methyl. In an alternative embodiment, $R_4$ is benzyl (i.e., the benzyl-substituted ene-carbamate).

The chiral catalyst preferably comprises a transition metal complex comprising the TolBINAP ligand. Suitably, the catalyst has the formula [(TolBINAP)Ru(arene)X']Y, [(TolBINAP)Ru(L)$_2$] or [(TolBINAP)Ru(L')$_2$X'$_2$], wherein X' is a singly-negative monodentate ligand, Y is a balancing anion, L is a monovalent negative coordinating ligand and L' is a non-ionic monodentate ligand.

The preferred TolBINAP ligand to be used in the asymmetric hydrogenation of the present invention is designated R-TolBINAP herein, and is shown in the structure below:

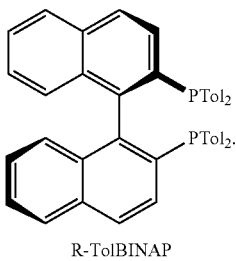

R-TolBINAP

The preferred catalyst has the formula:

[RuCl(R)-TolBINAP(arene)]Cl.

The most preferred catalysts are:

[RuCl(R)-TolBINAP(p-cymene)]Cl or [RuCl(R)-TolBINAP(C$_6$H$_6$)]Cl.

An alternative most preferred catalyst is Ru((R)-TolBINAP)Br$_2$.

[RuCl(R)-TolBINAP(p-cymene)]Cl can be prepared from (R)-TolBINAP and dichloro-(p-cymene)-ruthenium (II) dimer.

[RuCl(R)-TolBINAP(C$_6$H$_6$)]Cl can be prepared from [Ru(C$_6$H$_6$)Cl$_2$]$_2$ and (R)-TolBINAP in a 1:1 ethanol-dichloromethane mixture.

Ru((R)-TolBINAP)Br$_2$ can be prepared from Ru(2-methylallyl)$_2$COD, (R)-TolBINAP and HBr.

Preferably, the catalyst is produced in situ, i.e., the catalyst is not isolated prior to the hydrogenation reaction, but is formed from its precursor ligands in the reaction pot.

The hydrogenation is preferably carried out in the presence of an acid. Optionally, the acid is HBF$_4$, HCl, HBr, CF$_3$SO$_3$H, CH$_3$COOH or H$_3$PO$_4$. In a particularly advantageous aspect of the invention, the acid is H$_3$PO$_4$ at a concentration of 0.05% to 0.2%, preferably 0.1%. We have found that excellent conversion and ee can be obtained by the acid within this low concentration range. A concentration of 0.1% means that the weight of phosphoric acid in the mixture is equal to 0.1% of the weight of methanol (i.e., 0.1% w/w).

In an embodiment, the acid is present in a solvent. For example, the acid solvent is water. Preferably, the acid is H$_3$PO$_4$ and the solvent is an inert solvent(s) such as water. Suitably, the acid/solvent solution is 85% H$_3$PO$_4$ in water.

In an embodiment, the compound B/acid molar ratio ranges from 20/1 to 70/1. Suitably, the compound B/acid molar ratio ranges from 31/1 to 64/1. Preferably, the compound B/acid molar ratio ranges from 50/1 to 64/1. More preferably, the compound B/acid molar ratio is 64/1.

The improvements in the process according to the invention make it possible to obtain acceptable conversion and ee using a molar ratio of compound B/catalyst of 100/1 up to 2000/1. Preferably the molar ratio is 250/1 or greater, more preferably, 500/1 or greater, still more preferably 750/1 or greater. The molar ratio is most preferably in the range 1000/1, or greater, for example, about 2000/1.

The hydrogenation may be carried out in the presence of a solvent. For example, the hydrogenation solvent is selected from a substituted or unsubstituted straight- or branched-chain $C_1$ to $C_6$ alcohol, an arene or mixtures thereof. Optionally, the solvent is selected from MeOH, EtOH, $^i$PrOH, 1-PrOH, 1-BuOH, 2-BuOH, CF$_3$CH$_2$OH, DCM (dichloromethane), DCE (dichloroethane), THF (tetrahydrofuran), toluene or a 1:1 mixture of MeOH and DCM. It is particularly preferred that the hydrogenation takes place in a pre-distilled methanol solvent. In other words, the methanol is distilled before the catalyst is added to the hydrogenation reaction mass. The distillation may take place under a slow stream of an inert gas. It is thought that the distillation of the methanol, rather than degassing of the methanol, removes oxygen from the reaction vessel.

The hydrogenation may be carried out at a temperature ranging from above 70° C. to 100° C. Preferably, the hydrogenation is carried out at a temperature ranging from 75° C. to 90° C., more preferably at a temperature ranging from 75° C. to 85° C., and most preferably at a temperature of about 80° C. We have found that these particular temperature ranges are important for obtaining high yield and ee.

The hydrogenation may be carried out at a pressure ranging from 10 bars to 30 bars. Suitably, the hydrogenation is carried out at a pressure ranging from 20 bars to 30 bars. Preferably, the hydrogenation is carried out at a pressure of 30 bars.

In a preferred embodiment the catalyst is formed in situ. This means that the catalyst is formed from its ligands and is used in the process to convert compound B to compound A without an intervening purification step. Formation of the catalyst in DCM/EtOH has been found to provide a catalyst which produces the best conversion and ee.

In another aspect of the invention, the process further comprises subsequently recrystallising the compound of formula A. Although the recrystallisation may be carried out in a DCM/hexane mixture, in a particularly advantageous aspect of the invention, the recrystallisation is carried out in a 2-propanol/water mixture. We have unexpectedly found that recrystallisation in a 2-propanol/water mixture makes it possible to produce the product in a higher yield and with a higher ee.

The recrystallisation results in an ee ranging from 95 to 100%, preferably from 97 to 100%, more preferably from 99 to 100%.

The 2-propanol/water mixture preferably comprises 40-50 vol % 2-propanol and 50-60 vol % water, most preferably 45 vol % 2-propanol and 55 vol % water. The compound of formula A is preferably refluxed with the solvent, then cooled to 25-35° C., preferably 30° C., then cooled to approximately 5-10° C., preferably 5° C. Following cooling, the suspension may be filtered and the filter cake washed with a suitable solvent, for example, a mixture of 2-propanol/water. This washing step is advantageous in achieving high optical purity.

In an embodiment, compound A is in the form of the S enantiomer. In an alternative embodiment, compound A is in the form of the R enantiomer.

In a still further embodiment, the process further comprises converting the R or S enantiomer of compound A to the respective R or S enantiomer of a compound of formula C, or a salt thereof

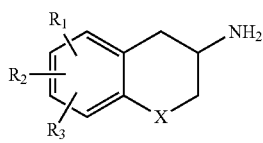

C wherein X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine.

Preferably, X is O. In a further embodiment, at least one of $R_1$, $R_2$ and $R_3$ is fluorine. Preferably the compound of formula C is:

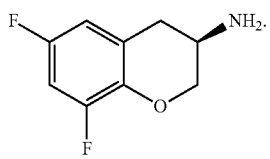 [SMILES: N[C@H]1COc2c(F)cc(F)cc2C1]

For example, the R or S enantiomer of compound A is converted to the respective R or S enantiomer of the compound of formula C by hydrolysis. Hydrolysis may be carried out using 40% potassium hydroxide in methanol, followed by isolation of the crude amine and crystallisation of the amine as a salt with L-tartaric acid.

Alternative methods of converting compound A to C are possible, depending on the nature of $R_4$. For example, the following processes may be used: mild acidic cleavage (in the presence of, for example, trifluoroacetic acid, HCl/EtOAc, or HBr/AcOH), acidic hydrolysis (strong aqueous acid with or without solvent), catalytic hydrogenolysis (Pd/C with a hydrogen source), etc. A comprehensive list of carbamates and methods for their cleavage can be found, for example, in Protective Groups in Organic Synthesis/Theodora W. Green and Peter G. M. Wuts, $2^{nd}$ ed., Wiley-Interscience 1991, p. 315-348.

In a yet further embodiment, the process further comprises reacting the R or S enantiomer of the compound of formula C, or a salt thereof, to produce the respective R or S enantiomer of a compound of formula E or a salt thereof.

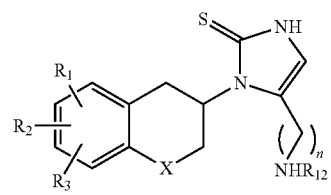

E wherein X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_{12}$ signifies hydrogen, alkyl or alkylaryl group, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine.

Preferably, X is O. In a further embodiment, at least one of $R_1$, $R_2$ and $R_3$ is fluorine.

In broad terms, the compound C can be converted to the compound E by using the compound C as an amino component to build the N(1) moiety of the substituted imidazole-2-thione ring of compound E. More specifically, the amino group on the compound C may be converted to a 5-substituted imidazole-2-thione ring, and the group substituted at the 5 position may be converted to the group $—(CH_2)_n—NHR_{12}$.

In one embodiment, the R or S enantiomer of the compound of formula C, or a salt thereof, is reacted with a compound of formula D1

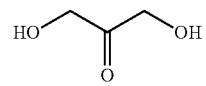

D1 to form a compound of formula D3

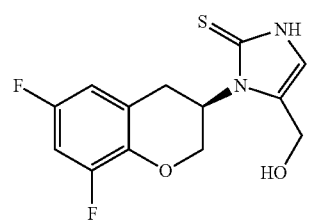

D3 followed by reaction of D3 with a dialkyl malonate and a base in the presence of a solvent, to form a compound of formula D4

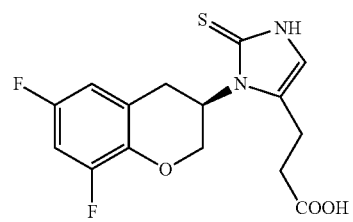

D4 followed by reaction of D4 with a suitable azide in the presence of a solvent, and then reaction with hydrochloric acid to form a compound of formula E.

In a further embodiment, the R or S enantiomer of the compound of formula C is reacted with a compound of formula D2

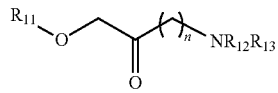
D2 to produce the respective R or S enantiomer of a compound of formula E or a salt thereof

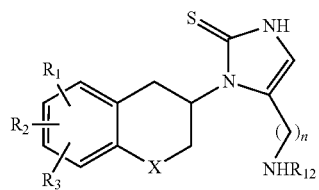
E where $R_1$, $R_2$ and $R_3$ are the same or different and signify hydrogens, halogens, alkyl, alkyloxy, hydroxy, nitro, alkylcarbonylamino, alkylamino or dialkylamino group; X is O, S or $CH_2$; n signifies 1, 2 or 3; $R_{12}$ signifies hydrogen, alkyl or alkylaryl group, $R_{11}$ signifies a hydroxyl protecting group and $R_{13}$ signifies an amino protecting group, or $R_{11}$ is defined as above but $R_{12}$ and $R_{13}$ taken together represent a phthalimido group; with a water soluble thiocyanate salt in the presence of an organic acid in a substantially inert solvent, followed by subsequent deprotection of the intermediate products F to I:

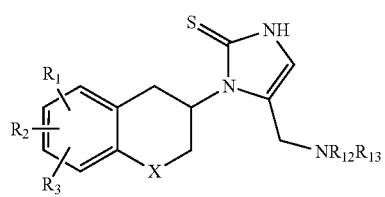
F

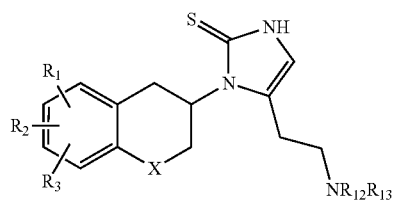
G

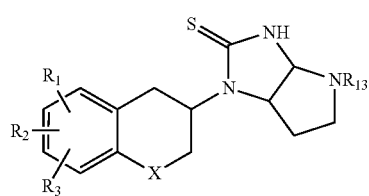
H

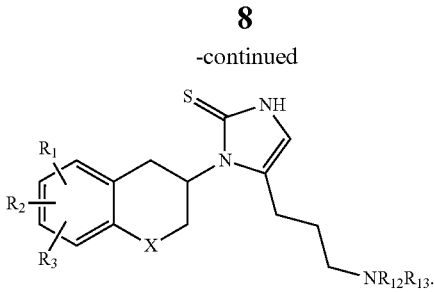
I

Preferably, the water soluble thiocyanate salt is an alkali metal thiocyanate salt or a tetraalkylammonium thiocyanate salt. Preferably, the solvent is an organic solvent. Further details, e.g., suitable reaction conditions may be found in WO 2004/033447.

In an embodiment, X is O. In another embodiment, n is 2 or 3. Preferably, X is O and n is 2 or 3. In a further embodiment, at least one of $R_1$, $R_2$ and $R_3$ is fluorine. Optionally, the product of the reaction of the R or S enantiomer of the compound of formula C and the compound of formula D is (S)-5-(2-aminoethyl)-1-(1,2,3,4-tetrahydronaphthalen-2-yl)-1,3-dihydroimidazole-2-thione; (S)-5-(2-aminoethyl)-1-(5,7-difluoro-1,2,3,4-tetrahydronaphthalen-2-yl)-1,3-dihydroimidazole-2-thione; (R)-5-(2-aminoethyl)-1-chroman-3-yl-1,3-dihydroimidazole-2-thione; (R)-5-(2-aminoethyl)-1-(6-hydroxychroman-3-yl)-1,3-dihydroimidazole-2-thione; (R)-5-(2-aminoethyl)-1-(8-hydroxychroman-3-yl)-1,3-dihydroimidazole-2-thione; (R)-5-(2-aminoethyl)-1-(6-methoxychroman-3-yl)-1,3-dihydroimidazole-2-thione; (R)-5-(2-aminoethyl)-1-(8-methoxychroman-3-yl)-1,3-dihydroimidazole-2-thione; (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-(2-aminoethyl)-1-(6-chloro-8-methoxychroman-3-yl)-1,3-dihydroimidazole-2-thione; (R)-5-(2-aminoethyl)-1-(6-methoxy-8-chlorochroman-3-yl)-1,3-dihydroimidazole-2-thione; (R)-5-(2-aminoethyl)-1-(6-nitrochroman-3-yl)-1,3-dihydroimidazole-2-thione; (R)-5-(2-aminoethyl)-1-(8-nitrochroman-3-yl)-1,3-dihydroimidazole-2-thione; (R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione; (R)-5-aminomethyl-1-(6-hydroxychroman-3-yl)-1,3-dihydroimidazole-2-thione; (R)-5-(2-aminoethyl)-1-(6-hydroxy-7-benzylchroman-3-yl)-1,3-dihydroimidazole-2-thione; (R)-5-aminomethyl-1-(6,8-difluorochroman-3-yl)-1,3-dihydroimidazole-2-thione; (R)-5-(3-aminopropyl)-1-(6,8-difluorochroman-3-yl)-1,3-dihydroimidazole-2-thione; (S)-5-(3-aminopropyl)-1-(5,7-difluoro-1,2,3,4-tetrahydronaphthalen-2-yl)-1,3-dihydroimidazole-2-thione; (R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione; (R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3- yl)-5-(2-methylaminoethyl)-1,3-dihydroimidazole-2-thione or (R)-1-chroman-3-yl-5-(2-methylaminoethyl)-1,3-dihydroimidazole-2-thione.

The product of the reaction of the R or S enantiomer of the compound of formula C and the compound of formula D may also be a salt of (S)-5-(2-aminoethyl)-1-(1,2,3,4-tetrahydronaphthalen-2-yl)-1,3-dihydroimidazole-2-thione; (S)-5-(2-aminoethyl)-1-(5,7-difluoro-1,2,3,4-tetrahydronaphthalen-2-yl)-1,3-dihydroimidazole-2-thione; (R)-5-(2-aminoethyl)-1-chroman-3-yl-1,3-dihydroimidazole-2-thione; (R)-5-(2-aminoethyl)-1-(6-hydroxychroman-3-yl)-1,3-dihydroimidazole-2-thione; (R)-5-(2-aminoethyl)-1-(8-hydroxychroman-3-yl)-1,3-dihydroimidazole-2-thione; (R)-5-(2-aminoethyl)-1-(6-methoxychroman-3-yl)-1,3-dihydroimidazole-2-thione; (R)-5-(2-aminoethyl)-1-(8-methoxychroman-3-yl)-1,3-dihydroimidazole-2-thione; (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-(2-aminoethyl)-1-(6-chloro-8-methoxychroman-3-yl)-1,3-dihydroimidazole-2-thione; (R)-5-(2-aminoethyl)-1-(6-methoxy-8-chlorochroman-3-yl)-1,3-dihydroimidazole-2-thione; (R)-5-(2-aminoethyl)-1-(6-nitrochroman-3-yl)-1,3-dihydroimidazole-2-thione; (R)-5-(2-aminoethyl)-1-(8-nitrochroman-3-yl)-1,3-dihydroimidazole-2-thione; (R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione; (R)-5-aminomethyl-1-(6-hydroxychroman-3-yl)-1,3-dihydroimidazole-2-thione; (R)-5-(2-aminoethyl)-1-(6-hydroxy-7-benzylchroman-3-yl)-1,3-dihydroimidazole-2-thione; (R)-5-aminomethyl-1-(6,8-difluorochroman-3-yl)-1,3-dihydroimidazole-2-thione; (R)-5-(3-aminoprop yl)-1-(6,8-difluorochroman-3-yl)-1,3-dihydroimidazole-2-thione; (S)-5-(3-aminoprop yl)-1-(5,7-difluoro-1,2,3,4-tetrahydronaphthalen-2-yl)-1,3-dihydroimidazole-2-thione; (R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione; (R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione. Preferably the salt is the hydrochloride salt.

Alternatively, the product of the reaction of the R or S enantiomer of the compound of formula C and the compound of formula D is the respective R or S enantiomer of the compound of formula P.

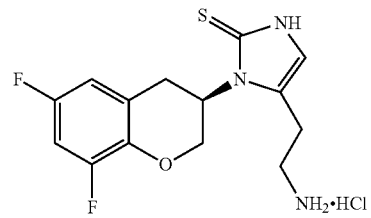

EXAMPLES

The invention will now be described with reference to the following examples.

Example 1

In order to find the best hydrogenation conditions, the following experiments have been performed on 0.6 g scale in MeOH (distilled under stream of Ar) at 80° C. and 30 bar $H_2$, reaction time 20 h:

| Catalyst | S/C | Additive | Conversion, % | Ee, % |
| --- | --- | --- | --- | --- |
| (R)-TolBINAP + [Ru(C$_6$H$_6$)Cl$_2$]$_2$ (formed in situ in DMF) | 1000 | no | 75 | 88 |
| (R)-TolBINAP + [Ru(C$_6$H$_6$)Cl$_2$]$_2$ (formed in situ in DMF) | 1000 | 0.1% w/w H$_3$PO$_4$ | 94 | 89 |
| (R)-TolBINAP + [Ru(C$_6$H$_6$)Cl$_2$]$_2$ (formed in situ in DCM-EtOH) | 1000 | no | 89 | 89 |
| (R)-TolBINAP + [Ru(C$_6$H$_6$)Cl$_2$]$_2$ (formed in situ in DCM-EtOH) | 1000 | 0.1% w/w H$_3$PO$_4$ | 100 | 90 |
| (R)-TolBINAP + [Ru(p-cymene)Cl$_2$]$_2$ (formed in situ in DCM-EtOH) | 1000 | 0.1% w/w H$_3$PO$_4$ | 100 | 89 |
| (R)-TolBINAP + Ru(methylallyl)$_2$COD (formed in situ in acetone) | 1000 | no | 98 | 90 |
| (R)-TolBINAP + Ru(methylallyl)$_2$COD (formed in situ in acetone) | 1000 | 0.1% w/w H$_3$PO$_4$ | 97 | 90 |

These results show that the presence of the acid additive at a concentration of 0.1% provided a significant improvement in conversion and ee.

The experiment with (R)-TolBINAP+[Ru(p-cymene)Cl$_2$]$_2$ formed in situ in DCM-EtOH was the most promising and was repeated 3 times to demonstrate reproducibility. All experiments gave 100% conversion and 89-89.4% ee.

To study the scalability of the process, experiments with 6 g and 24 g of the substrate have been performed, both giving complete conversion with 90% and 91% ee, respectively. For further process development, we used methanol from the shelf and degassed it by distilling off 10% of the solvent volume from the autoclave. The experiment was successful on 12 g scale, which was then repeated at 24 g and 50 g scale with a simultaneous increase of the substrate concentration from 0.25M to 0.5M. All experiments with non-distilled methanol gave 100% conversion and 91% ee. Attempts to further increase S/C ratio to 2000:1 did not give the complete conversion, although the conversion was quite high (99%).

Example 2

The product from the reaction was recrystallised in a 2-propanol-water mixture (45:55 v/v) and was unexpectedly found to produce an almost optically pure product (99.6-99.8% ee) in 88-89% yield. Some representative results are given below (all experiments at 80° C. and 30 bar hydrogen, non-optimised reaction time 20 h, substrate concentration 0.5M, 0.1% w/w $H_3PO_4$):

| Substrate weight, g | S/C | Conversion, % | Reaction mixture ee, % | Isolated yield, g (%) | Product ee, % |
|---|---|---|---|---|---|
| 50 | 1000 | 100 | 90.9 | 44.2 (88) | 99.7 |
| 50 | 1800 | 99.6 | 91.0 | 44.5 (88) | 99.7 |
| 40 | 2000 | 99.3 | 90.6 | 35.8 (89) | 99.7 |

Example 3

A process for the production of (R)-methyl 6,8-difluorochroman-3-ylcarbamate will now be described.

(1) Preparation of the Catalyst:

(R)-TolBINAP (0.152 g, 0.224 mmol) and dichloro(p-cymene)ruthenium(II) dimer (0.063 g, 0.104 mmol) were stirred in a Schlenk type apparatus (25 ml) in a mixture of ethanol (anhydrous, degassed by Ar bubbling for 0.5 h) (8 ml) and DCM (anhydrous, degassed by Ar bubbling for 0.5 h) (4 ml) at 45° C. (slow reflux) under Ar for 1.5 h, cooled to room temperature; the solution was used directly for hydrogenation.

(2) Reduction:

The substrate (50 g, 207 mmol) (6,8-difluoro-2H-chromen-3-yl)carbamic acid methyl ester) and MeOH (400 ml, not distilled) were charged in a 500 ml stainless steel autoclave, the autoclave was sealed and 40 ml of methanol was distilled off via the outlet tube with magnetic stirring. The outlet was closed without removal of the heating, the hydrogen pressure (7 bar) was applied and the solution was allowed to cool down to 25° C. with stiffing. 1% (w/w) $H_3PO_4$ in MeOH (40 ml, prepared from 85% aq $H_3PO_4$) was added via syringe with slow stream of hydrogen. The solution was degassed 5 times by applying and releasing the hydrogen pressure (20 bar) with stirring at 20-25° C. and the catalyst solution was added via syringe with a slow stream of hydrogen. The autoclave was closed, charged with hydrogen (30 bar) and heated at 80° C. (internal, thermocouple) with magnetic stirring for 20 h. The pressure was released after cooling to 20-25° C., 0.025 ml of the solution was diluted to 10 ml, the resulting solution was analysed directly by chiral HPLC.

The solution was evaporated to dryness under reduced pressure, the residue was dissolved in the mixture of 2-propanol and water (45:55 v/v, 335 ml) with stiffing under reflux, the solution was cooled with water to approx 30° C. (crystallisation occurred at 45° C.) with stirring, then with ice to 5° C. and stirred for 1 h at 5° C. The precipitate was collected on a sintered glass filter No. 2 (slow filtration occurred when filter paper was used), washed with the mixture of 2-propanol and water (45:55 v/v, 20-25° C., approx 75 ml), dried in vacuum at 50° C. to constant weight to give (R)-methyl 6,8-difluorochroman-3-ylcarbamate (44.2 g, 182 mmol, 88% yield).

It will be appreciated that the invention may be modified within the scope of the appended claims.

The invention claimed is:

1. A process for preparing the S or R enantiomer of a compound of formula A,

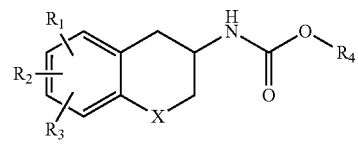

A the process comprising subjecting a compound of formula B to asymmetric hydrogenation in the presence of a chiral catalyst and a source of hydrogen,

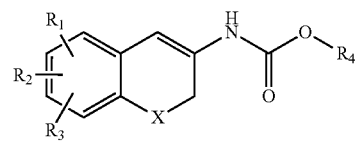

B wherein X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine, or iodine, wherein the chiral catalyst comprises a ligand which is the S or R enantiomer of TolBINAP and the reaction is carried out at a temperature from above 70° C. to 100° C. and in the presence of an acid at a concentration of 0.05 to 0.2%.

2. The process according to claim 1, wherein X is O.

3. The process according to claim 1, wherein at least one of $R_1$, $R_2$ and $R_3$ is fluorine.

4. The process according to claim 1, wherein compound A has the following formula:

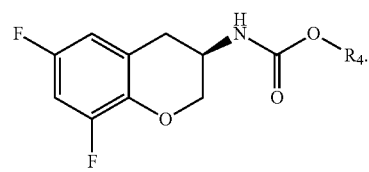

5. The process according to claim 1, wherein $R_4$ is $C_1$ to $C_4$ alkyl.

6. The process according to claim 5, wherein $R_4$ is methyl, ethyl or $^tBu$.

7. The process according to claim 6, wherein $R_4$ is methyl.

8. The process according to claim 1, wherein $R_4$ is benzyl.

9. The process according to claim 1, wherein the catalyst has the formula [(TolBINAP)Ru(arene)X']Y, [(TolBINAP)Ru(L)$_2$] or [(TolBINAP)Ru(L')$_2$X'$_2$], wherein X' is a singly-negative monodentate ligand, Y is a balancing anion, L is a doubly-negative bidentate ligand and L' is a non-ionic monodentate ligand.

10. The process according to claim 9, wherein the catalyst is [RuCl(R)-TolBINAP(arene)]Cl.

11. The process according to claim 9, wherein the catalyst is [RuCl(R)-TolBINAP(p-cymene)]Cl or [RuCl(R)-TolBINAP($C_6H_6$)]Cl or Ru((R)-TolBINAP)$Br_2$.

12. The process according to claim 1, wherein the acid is $H_3PO_4$.

13. The process according to claim 1, comprising forming the catalyst from its component ligands, then adding the catalyst to the hydrogenation reaction without any intermediate purification of the catalyst.

14. The process according to claim 13, wherein the component ligands are:
(R)-TolBINAP and [dichloro-(p-cymeme)-ruthenium(II)]$_2$;
(R)-TolBINAP and bis(2-methylallyl)(1,5-cyclooctadiene)ruthenium(II); or
(R)-TolBINAP and [Ru($C_6H_6$)$Cl_2$]$_2$.

15. A process for purifying a compound of formula A:

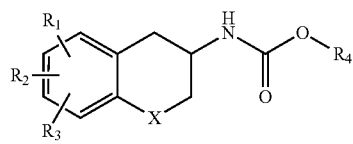

A wherein X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine, comprising recrystallisating compound A in as mixture of 2-propanol and water to produce compound A with an enantiomeric excess of from 95 to 100%.

16. A process for preparing the R or S enantiomer of a compound of formula C,

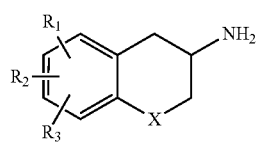

C wherein X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group; and $R_4$ is alkyl or aryl, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine, comprising forming the R or S enantiomer of a compound of formula A by a process according to claim 1, followed by converting the R or S enantiomer of the compound A to the respective R or S enantiomer of a compound of formula C.

17. A process for forming the R or S enantiomer of a compound of formula E or a salt thereof:

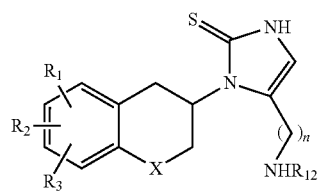

E $R_1$, $R_2$ and $R_3$ are the same or different and signify hydrogens, halogens, alkyl, alkyloxy, hydroxy, nitro, alkylcarbonylamino, alkylamino far dialkylamino group; X signifies O, S or $CH_2$; n signifies 1, 2 or 3; and $R_{12}$ signifies hydrogen, alkyl or alkylaryl group, comprising forming the R or S enantiomer of a compound of formula C according to the process of claim 16, and converting the R or S enantiomer of the compound of formula C to the R or S enantiomer of the compound of formula E.

18. The process according to claim 17, comprising reacting the R or S enantiomer of the compound of formula C with a compound of formula D2

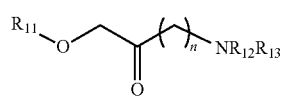

D2 where n signifies 1, 2 or 3; when n is 1 or 2, $R_{12}$ signifies hydrogen, alkyl or alkylaryl group; $R_{11}$ signifies a hydroxyl protecting group and $R_{13}$ signifies an amino protecting group; when n signifies 3, $R_{11}$ signifies a hydroxyl protecting group but $R_{12}$ and $R_{13}$ taken together represent a phthalimido group; and with a water soluble thiocyanate salt in the presence of an organic acid in a substantially insert solvent, followed by subsequent deprotection of the intermediate products F to I:

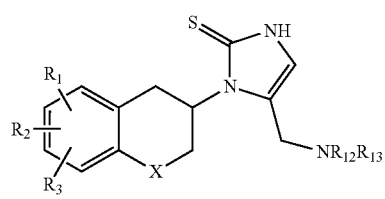

F

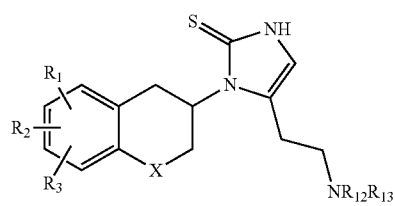

G

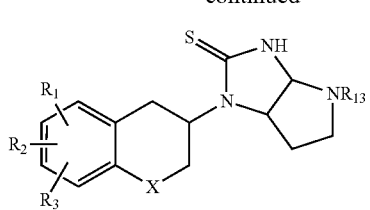

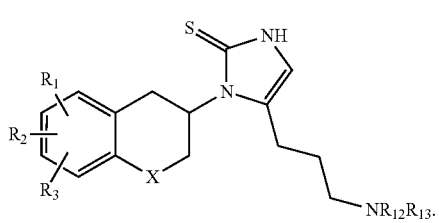

19. The process according to claim 17, wherein the compound E is (S)-5-(2-aminoethyl)-1-(1,2,3,4-tetrahydronaphthalen-2-yl)-1,3-dihydroimidazole-2-thione; (S)-5-(2-aminoethyl)-1-(5,7-difluoro-1,2,3,4-tetrahydronaphthalen-2-yl)-1,3-dihydroimidazole-2-thione; (R)-5-(2-aminoethyl)-1-chroman-3-yl-1,3-dihydroimidazole-2-thione; (R)-5-(2-aminoethyl)-1-(8-hydroxychroman-3-yl)-1,3-dihydroimidazole-2-thione; (R)-5-(2-aminoethyl)-1-(6-methoxychroman-3-yl)-1,3-dihydroimidazole-2-thione; (R)-5-(2-aminoethyl)-1-(8-methoxychroman-3-yl)-1,3-dihydroimidazole-2-thione; (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-(2-aminoethyl)-1-(6-chloro-8-methoxychroman-3-yl)-1,3-dihydroimidazole-2-thione; (R)-5-(2-aminoethyl)-1-methoxy-8-chlorochroman-3-yl)-1,3-dihydroimidazole-2-thione; (R)-5-(2-aminoethyl)-1-(6-nitrochroman-3-yl)-1,3-dihydroimidazole-2-thione; (R)-5-(2-aminoethyl)-1-(8-nitrochroman-3-yl)-1,3-dihydroimidazole-2-thione; (R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione; (R)-5-aminomethyl-1-(6-hydroxychroman-3-yl)-1,3-dihydroimidazole-2-thione; (R)-(2-aminoethyl)-1-(6-hydroxy-7-benzylchroman-3-yl)-1,3-dihydroimidazole-2-thione; (R)-5-aminomethyl-1-(6,8-difluorochroman-3-yl)-1,3-dihydroimidazole-2-thione; (R)-5-(3-aminopropyl)-1-(6,8-difluorochroman-3-yl)-1,3-dihydroimidazole-2-thione; (S)-5-(3-aminopropyl)-1-(5,7-difluoro-1,2,3,4-tetrahydronaphthalen-2-yl)-1,3-dihydroimidazole-2-thione; (R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione; (R)-5-(2-benzylaminoethyl)-1-(6-hydroxychroman-3-yl)-1,3-dihydroimidazole-2-thione; (R)-1-(6-hydroxychroman-3-yl)-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione, or a salt thereof.

20. The process according to claim 17, wherein the compound E is the respective R or S enantiomer of the compound of formula P:

21. The process of claim 15, wherein the compound A produced has an enantiomeric excess of from 97 to 100%.

* * * * *

UNITED STATES PATENT AND TRADEMARK OFFICE
CERTIFICATE OF CORRECTION

PATENT NO.        : 8,710,239 B2
APPLICATION NO.   : 12/990918
DATED             : April 29, 2014
INVENTOR(S)       : Alexander Beliaev and David Alexander Learmonth It is certified that error appears in the above-identified patent and that said Letters Patent is hereby corrected as shown below:

In the Claims

Column 13, Line 41, replace "in as mixture" with --in a mixture--

Column 15, Lines 25-26, replace
"(R)-5-(2-aminoethyl)-1-(8-hydroxychroman-3-yl)-1,3-dihydroimidazole-2-thione;" with
--(R)-5-(2-aminoethyl)-1-(6-hydroxychroman-3-yl)-1,3-dihydroimidazole-2-thione;
(R)-5-(2-aminoethyl)-1-(8-hydroxychroman-3-yl)-1,3-dihydroimidazole-2-thione;--

Column 15, Lines 42-43, replace
"(R)-5-(2-aminoethyl)-1-methoxy-8-chlorochroman-3-yl)-1,3-dihydroimidazole-2-thione;" with
--(R)-5-(2-aminoethyl)-1-(6-methoxy-8-chlorochroman-3-yl)-1,3-dihydroimidazole-2-thione;--

Column 16, Lines 19-20, replace
"(R)-1-(6-hydroxychroman-3-yl)-(2-methylaminoethyl)-1,3-dihydroimidazole-2-thione;" with
--(R)-1-(6-hydroxychroman-3-yl)-5-(2-methylaminoethyl)-1,3-dihydroimidazole-2-thione;--

Signed and Sealed this
First Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,710,239 B2
APPLICATION NO. : 12/990918
DATED : April 29, 2014
INVENTOR(S) : Beliaev et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 699 days.

Signed and Sealed this
Twenty-ninth Day of September, 2015

Michelle K. Lee
*Director of the United States Patent and Trademark Office*